United States Patent [19]

Wright

[11] 4,159,336
[45] Jun. 26, 1979

[54] META AND PARA PHENYLENEDI-5-ISOXAZOLE CARBOXYLIC ACIDS, ESTERS AND SALTS

[75] Inventor: John B. Wright, Kalamazoo, Mich.

[73] Assignee: The Upjohn Company, Kalamazoo, Mich.

[21] Appl. No.: 839,783

[22] Filed: Oct. 6, 1977

Related U.S. Application Data

[62] Division of Ser. No. 721,882, Sep. 10, 1976, Pat. No. 4,069,332.

[51] Int. Cl.² .................... A61K 31/42; C07D 261/18
[52] U.S. Cl. ................................. 424/272; 260/307 H
[58] Field of Search .................... 260/307 H; 424/272

[56] References Cited

U.S. PATENT DOCUMENTS 3,471,509  10/1909  McKillip .................. 260/307 G

OTHER PUBLICATIONS

Iwakura et al., Bull. Chem. Soc., Jap., 1968, 41 (7), 1648-1653.

*Primary Examiner*—Paul M. Coughlan, Jr.
*Attorney, Agent, or Firm*—Martin B. Barancik

[57] ABSTRACT

Compounds, compositions and methods of using the compounds of the formula as anti-allergics

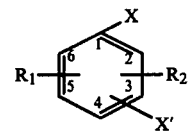

wherein X' is the same as X, X' is at the 3 or 4 position and is

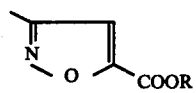

R is selected from the group consisting of hydrogen alkyl of one to eight carbon atoms, inclusive, and a physiologically acceptable metal or amine cation;
$R_1$ and $R_2$ are the same or different and are selected from the group consisting of hydrogen, alkyl of one to six carbon atoms, inclusive, alkoxy of one to six carbon atoms, inclusive, phenyl, cyano, nitro, trifluoromethyl, fluoro, chloro, and bromo, with the proviso that one of $R_1$ and $R_2$ is other than hydrogen.

12 Claims, No Drawings

META AND PARA PHENYLENEDI-5-ISOXAZOLE CARBOXYLIC ACIDS, ESTERS AND SALTS

CROSS REFERENCE TO RELATED APPLICATIONS

This application is a division of copending application Ser. No. 721,882, filed Sept. 10, 1976, U.S. Pat. No. 4,069,332.

BRIEF SUMMARY OF THE INVENTION

It has now been discovered that novel compounds of Formula I are useful in the prophylactic treatment of sensitized humans and animals for allergy and anaphylactic reactions of a reagin or non-reagin mediated nature. The compounds are formulated with pharmaceutical carriers for oral, parenteral, inhalation or rectal means of administration.

DETAILED DESCRIPTION OF THE INVENTION

In accordance with this invention, there are provided compounds represented by Formula I and hereafter referred to as Group A

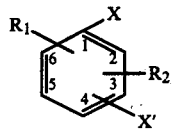

I wherein X' is at the 3 or 4 position, is the same as X, and is selected from the group consisting of

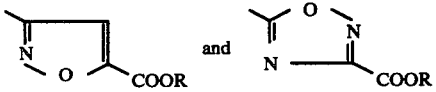

and wherein R is selected from the group consisting of hydrogen, alkyl of one to eight carbon atoms, inclusive, and a physiologically acceptable metal or amine cation, $R_1$ and $R_2$ are the same or different and are selected from the group consisting of hydrogen, alkyl of one to six carbon atoms, inclusive, alkoxy of one to six carbon atoms, inclusive, phenyl, cyano, nitro, trifluoromethyl, fluoro, chloro and bromo with the proviso that when X' is

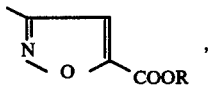

, one of $R_1$ and $R_2$ is other than hydrogen.

Another group of compounds, hereafter referred to as Group B, are those compounds of Group A wherein R is selected from the group consisting of hydrogen, alkyl of one to six carbon atoms, inclusive, and a physiologically acceptable metal or amine cation; $R_1$ and $R_2$ are the same or different and are selected from the group consisting of hydrogen, alkyl of one to four carbon atoms, inclusive, alkoxy of one to four carbon atoms, inclusive, phenyl, cyano, nitro, trifluoromethyl, fluoro, chloro and bromo with the proviso of Group A.

A further group of compounds, hereafter referred to as Group C, are those compounds of Group B wherein X' is at the 3-position, R is selected from the group consisting of hydrogen, alkyl of one to three carbon atoms, inclusive, a physiologically acceptable metal or amine cation, $R_1$ and $R_2$ are the same or different and are selected from the group consisting of hydrogen, alkyl of one to three carbon atoms, inclusive, alkoxy of one to three carbon atoms, inclusive, phenyl, cyano, trifluoromethyl, fluoro, chloro and bromo with the proviso of Group A.

A further group of compounds, hereafter referred to as Group D, are those compounds of Group C wherein $R_1$ and $R_2$ are the same or different and are selected from the group consisting of hydrogen, alkyl of one to three carbon atoms, inclusive, alkoxy of one to three carbon atoms, inclusive, cyano, trifluoromethyl, fluoro and chloro with the proviso of Group A.

Another group of compounds, hereafter referred to as Group E, are those compounds of Group D wherein $R_1$ and $R_2$ are at the 2 and 5 positions, respectively, with the proviso of Group A.

A still further group of compounds, hereafter referred to as Group F, are those compounds of Groups A, B, C, D, and E wherein X' is

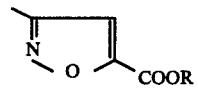

with the proviso of Group A.

Another group of compounds are those of Groups A, B, C, D, and E, wherein X' is

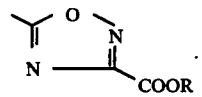

As employed in the above disclosure and throughout the specification and claims, the phrase "alkyl of one to eight carbon atoms, inclusive" includes methyl, ethyl, propyl, butyl, pentyl, hexyl, heptyl, octyl and isomers thereof. Illustrative examples of isomers are isopropyl, tert.butyl, neopentyl, 2,2-dimethylbutyl, isoheptyl and 2,2,4-trimethylpentyl. Alkyl of a smaller number of carbon atoms has a similar scoping. The term "halogen" includes fluoro, chloro, bromo, and iodo.

The phrase "physiologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

The term "physiologically acceptable metal" includes alkali metals such as sodium and potassium, alkaline earth metals such as calcium and magnesium, and other acceptable metals such as aluminum.

The compounds of the invention can be prepared by methods known in the art.

With respect to the 5-isoxazole carboxylates, acids and salts thereof, the appropriately $R_1$ and $R_2$ substituted iso or terephthaldehyde (II) is a suitable starting material. These compounds are reacted with an acid addition salt of hydroxylamine (III), for example, hydroxylamine hydrochloride under standard conditions to form a phthaldehyde-dioxime (IV). The phthaldehyde dioxime is then reacted with a halogen gas such as chlorine or bromine in an organic solvent inert to the gas at a low temperature to form the $\alpha,\alpha$-dihalophthaldehyde-dioxime (V). The product of formula V is then reacted with an alkyl propiolate (VI) in an organic solvent and an organic base to form the 5-isoxazolecarboxylate.

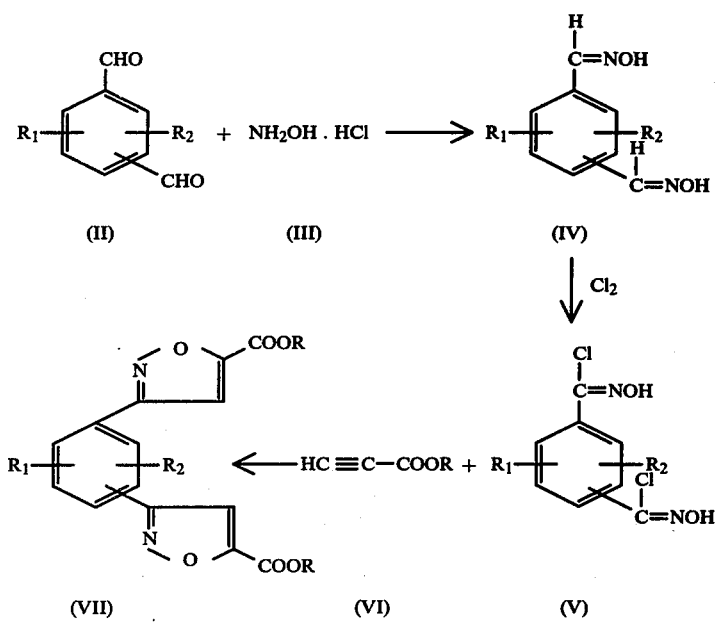

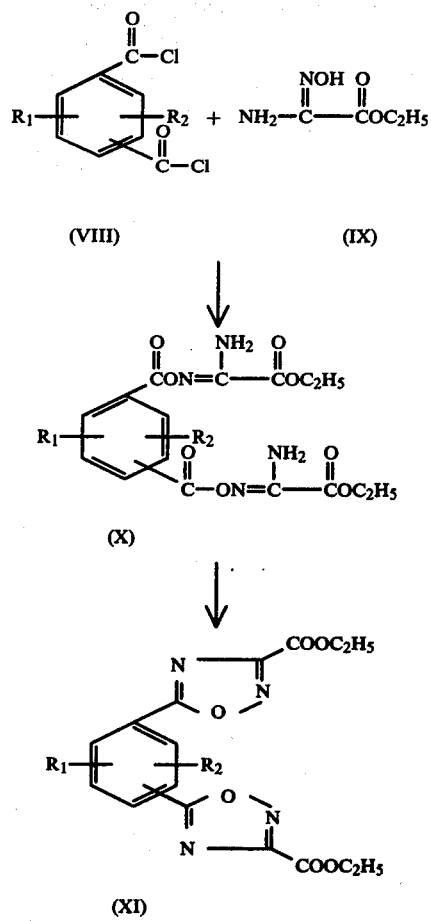

The 1,2,4-oxadiazole-3-carboxylates, acids and salts are readily prepared from the X and Y substituted iso or terephthalolyl dihalide, preferably chloride, starting material (VIII). This material is reacted with an alkyl-2-oximinooxamate such as ethyl-2-oximinooxamate (IX) in an inert organic solvent and a base to form a bis[(carbonyloxy)nitrilo]diglycinate (X). The diglycinate is then cyclized to a 1,2,4-oxadiazole-3-carboxylate (XI) by heat under vacuum.

The esters of formula VII or XI are readily transesterified to other esters of Formula I or converted to the acid or a physiologically acceptable salt by standard methods.

In preparing the 5-isoxazole carboxylates, the appropriately $R_1$ and $R_2$ substituted iso or tetephthaldehydes are prepared by conventional substitution methods. Depending upon the substituent itself, the placement of the substituent and the placement of the aldehyde group, the substitution of the benzene ring can occur on benzene itself, benzaldehyde, substituted benzaldehyde, the iso or terephthaldehyde or substituted iso or terephthaldehyde depending upon the orientation direction effect of the substituent. The appropriately substituted starting material is then reacted with an acid addition salt of hydroxylamine under standard conditions to form the iso or terephthaldehyde dioxime. The dioxime is reacted with a halogen gas, preferably chlorine, in an organic solvent inert to the gas at a low temperature to form the $\alpha,\alpha$-dihaloiso or terephthaldehyde-dioxime. Halogenated solvents such as carbon tetrachloride, chloroform and methylene chloride are suitable solvents for the halogenation step. The temperature of the reaction should be maintained from 0° to about 30° C., preferably from 0° to about 15° C. The $\alpha,\alpha$-dihalogenated dioxime is then reacted with an alkyl propiolate, alkyl having one to six carbon atoms, inclusive, in an organic solvent and an amine to form the 5-isoxazolecarboxylate. Suitable organic solvents are lower alcohols such as methanol, ethanol, propanol and the like, and cyclic ethers such as tetrahydrofuran and 1,4-dioxane. Suitable amines functioning as an acid scavenging agent are triethylamine, tripropylamine, and higher alkylamines, 1-methylpiperidine, 1-methylpyrrolidine, 1,4-dimethylpiperazine and the like.

The diesters are then converted to the diacids by alkaline hydrolysis with a base such as sodium hydroxide followed by treatment with an acid such as hydrochloric acid. The acid is then readily converted into any of the physiologically acceptable metal or amine salts.

In preparing the 1,2,4-oxadiazole-3-carboxylates, the appropriately $R_1$ and $R_2$ substituted iso or terephthalolyl dihalide starting materials are prepared from the corresponding dicarboxylic acid by reaction with an appropriate halogenating agent. The appropriately substituted di-carboxylic acids may be prepared from the corresponding iso or terephthaldehydes by oxidation. The $R_1$ and $R_2$ substituted iso or terephthalolyl di-halide is then reacted with an 2-R-oximinoooxamate, wherein R is alkyl of one to six carbon atoms, inclusive, in an inert organic solvent and a base. The solvent can be a lower ketone such as acetone, methylethyl ketone, methylisobutyl ketone and lower ethers, cyclic or open chain, such as 1,4-dioxane, tetrahydrofuran, and diethyl ether. The amine base, used as an acid scavenger, may be organic or inorganic, for example, sodium or potassium bicarbonate and triethylamine. The digyclinate formed in this step is then cyclized to the oxadiazole ester under a vacuum and from temperatures of 30°–100° C., depending upon the specific compound and the particular reduced pressure.

Following are illustrative examples of compounds of the invention which can be prepared by the known procedures.

TABLE I

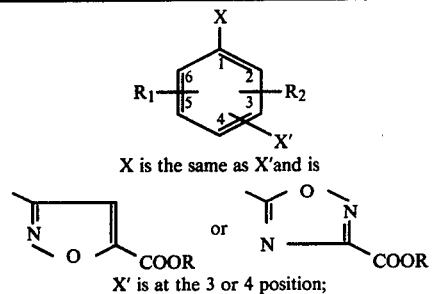

X is the same as X' and is $X'$ is at the 3 or 4 position; R is $C_2H_5$

| $R_1$ | $R_2$ | $X'$ |
|---|---|---|
| H | 2-CH₃ | 3 |
| H | 3-i-C₆H₁₃ | 4 |
| H | 5-t-C₄H₉ | 3 |
| H | 2-OC₂H₅ | 4 |
| H | 5-OC₅H₁₁ | 3 |
| H | 3-O-i-C₃H₇ | 4 |
| H | 4-OC₂H₅ | 3 |
| H | 5-C₆H₅ | 4 |
| H | 2-C₆H₅ | 3 |
| H | 3-CN | 4 |
| H | 2-CN | 3 |
| H | 2-NO₂ | 4 |
| H | 5-CN | 3 |
| H | 2-CF₃ | 4 |
| H | 5-NO₂ | 3 |
| H | 2-F | 4 |
| H | 2-CF₃ | 3 |
| H | 2-Cl | 4 |
| H | 5-F | 3 |
| H | 2-Br | 4 |
| H | 2-Cl | 3 |
| 2-Cl | 5-CF₃ | 3 |
| H | 5-Br | 3 |
| 2-Cl | 3-Cl | 4 |
| 2-Cl | 5-CN | 3 |
| 3-F | 5-NO₂ | 4 |
| 2-CH₃ | 5-O-i-C₄H₉ | 3 |
| 2-C₂H₅ | 3-i-C₃H₇ | 4 |
| 2-CN | 5-C₆H₅ | 3 |
| 3-Br | 5-Br | 4 |
| 2-OC₂H₅ | 5-OC₄H₉ | 3 |
| 3-C₅H₁₁ | 5-Cl | 4 |
| 2-CN | 5-CN | 3 |
| 2-CH₃ | 3-OCH₃ | 4 |
| 2-Cl | 4-CN | 3 |
| 2-C₆H₅ | 5-CF₃ | 4 |
| 4-Br | 6-Br | 3 |
| 2-C₃H₇ | 5-NO₂ | 4 |
| 2-F | 5-O-i-C₃H₇ | 3 |
| 2-C₂H₅ | 3-C₂H₅ | 4 |

TABLE II

The compounds of Table I are converted to esters wherein R is alkyl of one to eight carbon atoms, inclusive, other than ethyl. Examples of such esters are methyl, propyl, butyl, pentyl, hexyl, heptyl, octyl and isomers thereof.

TABLE III

The compounds of Table I are converted to the diacids by standard methods.

TABLE IV

The compounds of Table III are converted to physiologically acceptable salts of the acid, preferably sodium, potassium and tris(hydroxymethyl)aminomethane.

Tables II, III and IV are not rendered in the same manner as Table I for the purpose of brevity. However, the same scoping is intended.

The following examples are compounds in accordance with this invention and compounds which can be formulated into pharmaceutical compositions of the invention. The compounds are not intended to limit but merely to exemplify the invention.

EXAMPLE 1

3,3'-m-Phenylenedi-5-isoxazolecarboxylic acid a.—Diethyl 3,3'-m-phenylenedi-5-isoxazolecarboxylate

To a stirred solution of 4.66 g. (0.02 mole) of α,α-dichloroisophthaldehyde dioxime in 75 ml. of tetrahydrofuran is added 4.32 g. (0.044 mole) of ethyl propiolate. The solution is cooled to 0° in an ice-bath and there is added 4.04 g. (0.04 mole) of triethylamine. The ice-bath is removed and the reaction mixture allowed to stand at room temperature overnight.

The precipitate is removed by filtration. The filtrate is evaporated to dryness in vacuo. The combined residue is boiled in 250 ml. of ethanol and the insoluble material removed by filtration. There is obtained 2.20 g. of a colorless solid melting at 185°–186°.

Analysis: Calc'd for $C_{18}H_{16}N_2O_6$: C, 60.67; H, 4.53; N, 7.86; Found: C, 60.55; H, 4.78; N, 7.64.

The infrared and NMR spectra are in agreement.

b.—3,3'-m-Phenylenedi-5-isoxazolecarboxylic acid

A mixture of 1.50 g. (0.004 mole) of diethyl 3,3'-m-phenylenedi-5-isoxazolecarboxylate and 0.5 gm. of sodium hydroxide in 100 ml. of water is refluxed for ninety minutes.

The solution is cooled and acidified with hydrochloric acid. The precipitate is removed by filtration and washed with water. There is obtained 900 mg. of colorless solid melting at 282° (dec.).

Analysis Calc'd for $C_{14}H_8N_2O_6 \cdot H_2O$: C, 52.83; H, 3.16; N, 8.80; $H_2O$, 5.65; Found: C, 52.40; H, 2.94; N, 8.40; $H_2O$, 5.86.

The NMR spectrum is in agreement.

The hydrate may be readily dehydrated to the anhydrous form by conventional methods.

EXAMPLE 2

Diethyl 5,5'-m-phenylenebis-1,2,4-oxadiazole-3-carboxylate a.—Ethyl 2-thiooxamate

A solution of 50 gm. (0.5 mole) of ethylcyanoformate in 60 ml. of dry benzene is cooled to 0° in an ice-bath. Hydrogen sulfide is bubbled into the solution for two hours. To the saturated solution there is added 0.5 gm. of diethylamine. The temperature rises to 25°. The reaction mixture is allowed to stand at room temperature overnight. The precipitate is removed by filtration. There is obtained 11.2 gm. of yellow crystals melting at 64°–65° C. The filtrate is evaporated to dryness in vacuo and the residue recrystallized from benzene-cyclohexane. There is obtained an additional 23 gm. of material melting at 64°–66° C. The total yield is 34.2 gm. (53%).

b. Ethyl 2-oximinooxamate

The procedure of W. K. Warburton, J. Chem. Soc. (c) 1966, 1522-4 is followed.

A solution of 8.98 gm. (0.39 mole) of sodium in 180 ml. of anhydrous ethanol is added to a solution of 26.8 gm. (0.386 mole) of hydroxylamine hydrochloride in 270 ml. of hot ethanol. The precipitate is removed by filtration. To the stirred filtrate is added 34.2 gm. (0.26 mole) of ethyl 2-thiooxamate. The yellow solution is allowed to stand overnight. The solution is evaporated to dryness in vacuo and the residue recrystallized from diethyl ether. There is obtained 21.2 g. (68%) of a yellow solid melting at 99°–101° C.

c.—Diethyl 2,2'[m-phenylenebis([carbonyloxy]-nitrilo)]diglycinate

A mixture of 13.86 gm. (0.105 mole) of ethyl 2-oximinooxamate, 8.3 g. (0.054 mole) of potassium carbonate and 75 ml. of acetone is stirred at room temperature. To the mixture there is added a solution of 10.15 gm. (0.05 mole) of isophthaloyl dichloride in 50 ml. of acetone. The reaction mixture is allowed to stand for three days at room temperature.

The precipitate is removed by filtration and stirred in 450 ml. of water. The insoluble material is removed by filtration. There is obtained 13.8 gm. (70%) of a colorless solid melting at 209°–210° C.

Analysis: Calc'd for $C_{16}H_{18}N_4O_8$: C, 48.73; H, 4.60; N, 14.21; Found: C, 48.86; H, 4.58; N, 13.76

The infrared and NMR spectra are in agreement.

d.—Diethyl 5,5'-m-phenylenebis-1,2,4-oxadiazole-3-carboxylate

Seven and eighty eight hundredths grams diethyl 2,2'-[m-phenylenebis([carbonyloxy]nitrilo)]diglycinate [7.88 gm (0.02 mole)] is placed in a round bottom flask and 18 mm. of vacuum applied. The solid is heated to a molten liquid for thirty minutes and allowed to cool to room temperature. The solid residue is boiled with ethanol, cooled to room temperature and refrigerated. The solid is removed by filtration. There is obtained 4.15 g. (60%) of tan solid melting at 159°–160° C.

Analysis: Calc'd for $C_{16}H_{14}N_4O_6$: C, 53.63; H, 3.94; N, 15.64; Found: C, 53.45; H, 3.99; N, 16.17

The infrared and NMR spectra are in agreement.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula I. The preferred method of administration is by inhalation into the lung or nose by means of an aerosol liquid or powder for insufflation. It should be noted that the proviso relating to the compounds in Formula I does not apply to the compositions or methods of use. The unsubstituted 5-isoxazole carboxylic compounds are suitable for composition and methods of use.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung or nose and containing a compound of the invention which is water-soluble. For treatment of allergic conditions of the nose, such as rhinitis, compositions adapted for contact with nasal linings are preferred.

Compositions for inhalation are of three basic types: (1) a powder mixture preferably micropulverized with particle size preferably from about 1 to about 5 microns; (2) an aqueous solution to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhalted through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as—ethyl, or propyl chlorides. Further suitable liquefied propellants are the fluorinated and fluorochlorinated lower alkanes such as are sold under the trademarks "Freon" and "Genetron." Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form," as used in the specification and claims, refers to physically discrete units suitable as unitary dosages for human subjects and animals, each unit containing a predetermined quantity of active material calculated to produce the desired therapeutic effect. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.1 to about 20 mg. of compound in a single dose, administered parenterally or by inhalation in the compositions of this invention are effective for preventing allergy attacks. More specifically, the single dose is from about 0.1 to about 5 mg. of compound. The oral and rectal dose is from about 5 to about 50 mg. in a single dose. More specifically, the single dose is from about 10 to about 25 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until the dosage no longer provides effective protection. At that time, the larger dosage is repeated, followed by the reduced dosage. An example of such a dosage schedule is the following: An asthmatic individual insufflates 10 mg. of disodio 5,5'-m-phenylenebis-1,2,4-oxaziadole-3-carboxylate. Four hours later, the individual insufflates 0.2 mg. of the same compound and every four to six hours thereafter insufflates 0.2 mg. of the same compound until effective asthma prophylaxis is not provided. The individual then insufflates 10 mg. of the same compound, then reduces the insufflation dosage to 0.2 mg. four to six hours later. The dosage schedule continues in this manner.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, uticaria, auto-immune diseases, exercise induced asthma, stress induced asthma, systemic anaphylaxis, and bird fancier's disease. Preferred are the reagin mediated conditions such as bronchial asthma, allergic rhinitis, food allergy, uticaria, and allergic vernal kerato conjunctivitis.

EXAMPLE 3

A lot of 10,000 tablets, each containing 50 mg. of diethyl 3,3'-m-phenylenedi-5-isoxazolecarboxylate is prepared from the following types and amounts of ingredients:
  Diethyl 3,3'-m-phenylenedi-5-isoxazolecarboxylate—500 Gm.
  Dicalcium phosphate—1,000 Gm.
  Methylcellulose, U.S.P. (15 cps)—60 Gm.
  Talc—150 Gm.
  Corn Starch—200 Gm.
  Magnesium stearate—10 Gm.

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of one tablet every four to six hours.

EXAMPLE 4

One thousand two-piece hard gelatin capsules, each containing 50 mg. of diethyl 5,5'-m-phenylenebis-1,2,4-oxadiazole-3-carboxylate are prepared from the following types and amounts of ingredients:
  Diethyl 5,5'-m-phenylenebis-1,2,4-oxadiazole-3-carboxylate—50 Gm.
  Talc—50 Gm.
  Lactose—100 Gm.
  Magnesium stearate—1 Gm.

The ingredients are mixed well and filled into capsules of the proper size.

Capsules so prepared are useful in preventing attacks of bronchial asthma at a dose of one capsule every four to six hours.

EXAMPLE 5

One thousand tablets, each containing 5 mg. of diethyl 3,3'-m-phenylenedi-5-isoxazolecarboxylate are prepared from the following types and amounts of ingredients:
  Diethyl 3,3'-m-phenylenedi-5-isoxazolecarboxylate—5 Gm.
  Microcrystalline cellulose NF—410 Gm.
  Starch—100 Gm.
  Magnesium stearate powder—3 Gm.

The ingredients are screened and blended together and pressed into tablets.

The tablets are useful to protect against food allergy at a dose of one tablet before meals.

EXAMPLE 6

One thousand tablets, each containing 20 mg. of diethyl 5,5'-m-phenylenebis-1,2,4-oxadiazole-3-carboxylate are prepared from the following types and amounts of ingredients:
  Diethyl 5,5'-m-phenylenebis-1,2,4-oxadiazole-3-carboxylate—20 Gm.
  Microcrystalline cellulose NF—410 Gm.
  Starch—100 Gm.
  Magnesium stearate powder—3 Gm.

The ingredients are screened and blended together and pressed into tablets.

The tablets are useful to protect against food allergy at a dose of one tablet before meals.

EXAMPLE 7

A sterile preparation suitable for intramuscular injection and containing 20 mg. of di-tris(hydroxymethyl)aminomethane (THAM) salt of 5,5'-m-phenylenebis-1,2,4-oxadiazole-3-carboxylic acid in each milliliter is prepared from the following ingredients:
  diTHAM salt of 5,5'-m-phenylenebis-1,2,4-oxadiazole-3-carboxylic acid—20 Gm.
  Benzyl benzoate—200 ml.
  Methylparaben—1.5 Gm.
  Propylparaben—0.5 Gm.
  Cottonseed oil q.s.—1,000 ml.

One milliliter of this sterile preparation is injected for prophylactic treatment of allergic rhinitis or urticaria.

EXAMPLE 8

Six hundred ml. of an aqueous solution containing 5.0 mg. of the diTHAM salt of 5,5'-m-phenylenebis-1,2,4-oxadiazole-3-carboxylic acid per ml. is prepared as follows:
  diTHAM salt of 5,5'-m-phenylenebis-1,2,4-oxadiazole-3-carboxylic acid—3.0 Gm.
  Sodium chloride—5 Gm.
  Water for injection q.s.—600 ml.

The THAM salt and sodium chloride are dissolved in sufficient water to make 600 ml. and sterile filtered.

The solution is placed in nebulizers designed to deliver 0.25 ml. of solution per spray.

The solution is inhaled into the lungs every four to six hours for prevention of asthmatic attacks.

EXAMPLE 9

A powder mixture consisting of 2 grams of disodio 5,5'-m-phenylenebis-1,2,4-oxadiazole-3-carboxylate and sufficient lactose to make five grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 10

Twelve grams of an aerosol composition are prepared from the following ingredients:
diTHAM salt of 5,5'-m-phenylenebis-1,2,4-oxadiazole-3-carboxylic acid—1.00 Gm.
Freon 12—1.44 Gm.
Freon 114—2.16 Gm.
Water—6.80 Gm.
Sorbitan monooleate—0.60 Gm.

The THAM salt is dissolved in the water and added to the Freons. The twelve grams of compositions are added to a 13 cc plastic coated bottle and capped with a metering valve. The metering valve releases 80 mg. of composition in an aerosol. The aerosol is inhaled every four to six hours for prevention of asthmatic attacks.

EXAMPLE 11

In individuals who require continual treatment in the Examples 3 through 10, the dosage of the Example is given initially and each succeeding administration of the drug is at 1/50 of the initial dosage. This maintenance dosage is continued until effective allergy prophylaxis is not obtained. The initial dosage of Examples 3 through 10 is then started once more, followed by the maintenance dosages.

EXAMPLE 12

After allowing for the different solubilities of the compounds and the activity of the particular compound as measured, for example, by the in vivo rat passive cutaneous anaphylaxis assay, a suitable quantity of each of the compounds of Table I through Table IV and Examples 1–2, is substituted for the active compound in the compositions and uses of Examples 3 through 11. Results showing anti-allergy activity are obtained.

EXAMPLE 13

The rat passive cutaneous anaphylaxis assay is executed in the following manner:

Female Sprague-Dawley 250 gm. rats are skin-sensitized with rat anti-ovalbumin homocytotropic antibody that is heat labile and has a passive cutaneous anaphylaxis titer of 1:128. After a 72 hour latency period, the animals are challenged i.v. with 4 mg. ovalbumin (OA)+5 mg. Evans blue dye and the test compound. Where the test compound is insufficiently soluble in an appropriate vehicle to be administered i.v., the compound is administered orally from five to sixty minutes prior to antigen challenge. Thirty minutes later the extravascular bluing that results from antigen antibody combination at the skin site is used. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

Diethyl 5,5'-m-phenylenebis-1,2,4-oxadiazole-3-carboxylate is tested orally by the above procedure in the rat passive cutaneous anaphylaxis assay.

50 mg./kg. of the above-identified compound provided the following inhibitions at 5, 20 and 60 minutes: 61, 56 and 34 percent inhibition.

I claim:

1. A compound of the formula

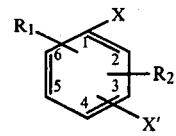

wherein X' is the 3 or 4 position, is the same as X and is

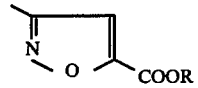

wherein R is selected from the group consisting of hydrogen, alkyl of one to eight carbon atoms, inclusive, and a physiologically acceptable metal or amine cation; $R_1$ and $R_2$ are the same or different and are selected from the group consisting of hydrogen, alkyl of one to six carbon atoms, inclusive, alkoxy of one to six carbon atoms, inclusive, phenyl, cyano, nitro, trifluoromethyl, fluoro, chloro, and bromo, with the proviso that one of $R_1$ and $R_2$ is other than hydrogen.

2. A compound in accordance with claim 1 wherein R is selected from the group consisting of hydrogen, alkyl of one to six carbon atoms, inclusive, and a physiologically acceptable metal or amine cation; $R_1$ and $R_2$ are the same or different and are selected from the group consisting of hydrogen, alkyl of one to four carbon atoms, inclusive, alkoxy of one to four carbon atoms, inclusive, phenyl, cyano, nitro, trifluoromethyl, fluoro, chloro, and bromo.

3. A compound in accordance with claim 2 wherein X' is at the 3-position, R is selected from the group consisting of hydrogen, alkyl of one to three carbon atoms, inclusive, a physiologically acceptable metal or amine cation, $R_1$ and $R_2$ are the same or different and are selected from the group consisting of hydrogen, alkyl of one to three carbon atoms, inclusive, alkoxy of one to three carbon atoms, inclusive, phenyl, cyano, trifluoromethyl, fluoro, chloro and bromo.

4. A compound in accordance with claim 3 wherein $R_1$ and $R_2$ are the same or different and are selected from the group consisting of hydrogen, alkyl of one to three carbon atoms, inclusive, alkoxy of one to three carbon atoms, inclusive, cyano, trifluoromethyl, fluoro and chloro.

5. A compound in accordance with claim 4 wherein $R_1$ and $R_2$ are at the 2 and 5 positions, respectively.

6. A pharmaceutical composition comprising an antireagin or non-reagin mediated allergy effective amount of a compound of the formula

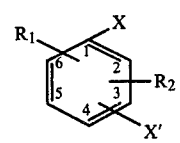

wherein X' is at the 3 or 4 position, is the same as X and is

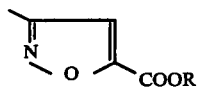

wherein R is selected from the group consisting of hydrogen, alkyl of one to eight carbon atoms, inclusive, and a physiologically acceptable metal or amine cation;

$R_1$ and $R_2$ are the same or different and are selected from the group consisting of hydrogen, alkyl of one to six carbon atoms, inclusive, alkoxy of one to six carbon atoms, inclusive, phenyl, cyano, nitro, trifluoromethyl, fluoro, chloro, and bromo in association with a pharmaceutical carrier.

7. A composition in accordance with claim 6 wherein the compound is diethyl 3,3'-m-phenylenedi-5-isoxazolecarboxylate.

8. A composition in accordance with claim 6 wherein the compound is 3,3'-m-phenylenedi-5-isoxazolecarboxylic acid.

9. A process for the prophylactic treatment of allergy of a reagin or non-reagin mediated nature in a mammal which comprises administering to a mammal in need of said treatment an effective amount of a compound of the formula

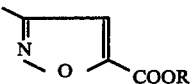

wherein X' is at the 3 or 4 position, is the same as X, and is wherein R is selected from the group consisting of hydrogen, alkyl of one to eight carbon atoms, inclusive, and a physiologically acceptable metal or amine cation;

$R_1$ and $R_2$ are the same or different and are selected from the group consisting of hydrogen, alkyl of one to six carbon atoms, inclusive, alkoxy of one to six carbon atoms, inclusive, phenyl, cyano, nitro, trifluoromethyl, fluoro, chloro, and bromo.

10. A process in accordance with claim 9 wherein the compound is diethyl 3,3'-m-phenylenedi-5-isoxazolecarboxylate.

11. A process in accordance with claim 9 wherein the compound is 3,3'-m-phenylenedi-5-isoxazolecarboxylic acid.

12. A process in accordance with claim 9 wherein a dosage form of tablet, capsule, powder for insufflation, or aerosol for inhalation is administered.

* * * * *